United States Patent [19]

Steppan et al.

[11] Patent Number: 5,217,845

[45] Date of Patent: Jun. 8, 1993

[54] PHOTOPOLYMERIZABLE MIXTURE AND PHOTOPOLYMERIZABLE COPYING MATERIAL CONTAINING SAME

[75] Inventors: Hartmut Steppan; Hans-Dieter Frommeld, both of Wiesbaden, Fed. Rep. of Germany

[73] Assignee: Hoechst Aktiengesellschaft, Frankfurt am Main, Fed. Rep. of Germany

[21] Appl. No.: 766,975

[22] Filed: Sep. 26, 1991

Related U.S. Application Data

[63] Continuation of Ser. No. 454,198, Dec. 21, 1989, abandoned.

[30] Foreign Application Priority Data

Dec. 22, 1988 [DE] Fed. Rep. of Germany ....... 3843204

[51] Int. Cl.$^5$ .............................................. G03F 7/031
[52] U.S. Cl. .................................. 430/281; 430/273; 430/915; 430/916; 522/63
[58] Field of Search ............... 430/281, 915, 916, 273; 522/26, 63

[56] References Cited

U.S. PATENT DOCUMENTS

| | | | |
|---|---|---|---|
| 3,751,259 | 8/1973 | Bauer et al. | 96/115 P |
| 4,587,200 | 5/1986 | Tamoto et al. | |
| 4,845,011 | 7/1989 | Wilczak et al. | 522/26 |
| 4,940,648 | 7/1990 | Geiger | 522/26 |

FOREIGN PATENT DOCUMENTS 374705 6/1990 European Pat. Off. .

OTHER PUBLICATIONS

The Journal of Organic Chemistry, vol. 29, Sep.–Dec. 1964, p. 2857.
Journal of the Chemical Society, Section C Organic Chemistry, 1967, p. 2071.
Journal of the Chemical Society, Section C Organic Chemistry, 1968, p. 2900.

Primary Examiner—Marion E. McCamish
Assistant Examiner—Christopher D. Rodee
Attorney, Agent, or Firm—Foley & Lardner

[57] ABSTRACT

A photopolymerizable mixture is described which contains a polymeric binder, a polymerizable compound and an acridine compound of the general formula I

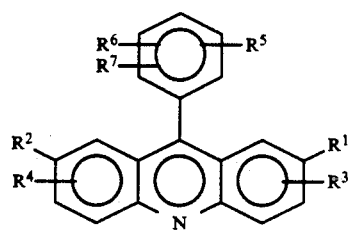

as photoinitiator, in which
$R^1$ denotes an optionally substituted alkyl or acyl group,
$R^2$, $R^3$ are identical or different and denote and $R^4$ hydrogen or halogen atoms or optionally substituted alkyl or acyl groups,
$R^5$, $R^6$ are identical or different and denote and $R^7$ hydrogen or halogen atoms or optionally substituted alkyl, aryl or acyl groups, or groups of the formula II

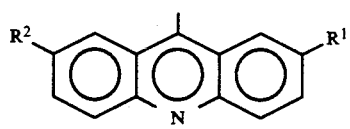

The photoinitiators yield a mixture having high photosensitivity and have a lower tendency to diffusion than the known 9-phenylacridine.

15 Claims, No Drawings

PHOTOPOLYMERIZABLE MIXTURE AND PHOTOPOLYMERIZABLE COPYING MATERIAL CONTAINING SAME

This application is a continuation, of application Ser. No. 07/454,198, filed Dec. 21, 1989 now abandoned.

BACKGROUND OF THE INVENTION

The invention relates to a photopolymerizable mixture. More particularly, the invention relates to a mixture which comprises a polymeric binder, a polymerizable compound having at least one terminal olefinic double bond and having a boiling point above 100° C. at normal pressure, and a 9-arylacridine compound as photoinitiator.

DE-C-2,027,467 discloses photopolymerizable mixtures of the composition specified above which contain derivatives of acridine and phenazine as photoinitiators. Some representatives of this class of compound, for example 9-phenylacridine, are notable for a high photosensitivity. The preferred representatives have the disadvantage that they tend to migrate out of photopolymerizable coatings which are in contact with polyethylene films into said films and through them. As a result, the coating becomes depleted of initiator and loses sensitivity. The initiator may also migrate out of photocured photoresist coatings into certain treatment baths, for example acidic electroplating baths and produce a troublesome yellow coloration therein.

SUMMARY OF THE INVENTION

Accordingly, it is an object of the present invention to provide a photopolymerizable mixture having a photosensitivity and image reproduction as good as the preferred known mixtures, but with photoinitiators having a lesser tendency to migrate out of the photopolymerizable or photopolymerized coating.

In accomplishing the foregoing objectives, there has been provided, in accordance with one aspect of the present invention, a photopolymerizable mixture which comprises a polymeric binder, a polymerizable compound having at least one terminal olefinic double bond and having a boiling point above 100° C. at normal pressure, and a 9-phenylacridine compound as photoinitiator, wherein the acridine compound conforms to the general formula I

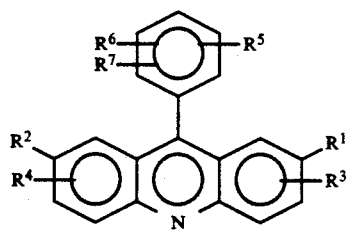

(I)

in which
R$^1$ denotes an optionally substituted alkyl or acyl group,
R$^2$, R$^3$ are identical or different and denote
and R$^4$ hydrogen or halogen atoms or optionally substituted alkyl or acyl groups,
R$^5$, R$^6$ are identical or different and denote
and R$^7$ hydrogen or halogen atoms or optionally substituted alkyl, aryl or acyl groups, or groups of the formula II

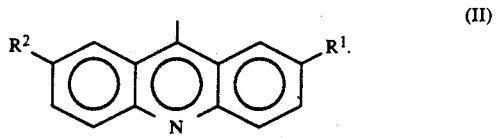

(II)

In accordance with another aspect of the present invention, there is provided a photopolymerizable copying material which comprises a coating base and a photopolymerizable layer comprising the photopolymerizable mixture defined above.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF PREFERRED EMBODIMENTS

In the compounds of the general formula I, R$^1$ is an alkyl group containing preferably 1 to 10 carbon atoms, an aliphatic acyl group containing 2 to 10 carbon atoms or an aromatic acyl group containing 7 to 15 carbon atoms.

These groups may be substituted by halogen atoms, in particular fluorine, chlorine or bromine, hydroxyl groups, alkoxy groups, alkoxycarbonyl groups, alkyl groups, aryl groups, aryloxy groups, acyl groups, acyloxy groups, primary, secondary or tertiary amino groups, alkoxycarbonylamino groups or alkylaminocarbonyloxy groups. In general R$^1$ has a molecular weight of about 15 to 200, preferably of 60 to 150. R$^2$ is a hydrogen or halogen atom or a group having the meaning of R$^1$.

Preferably R$^2$ is a group having the meaning of R$^1$, it being possible for R$^1$ and R$^2$ to be identical or different.

R$^3$ and R$^4$ have the same general meaning as R$^2$, but preferably at least one of these radicals is a hydrogen atom.

R$^5$, R$^6$ and R$^7$ may have the same meaning as R$^3$ and R$^4$ and may additionally be aryl groups or groups of the formula II, in particular halogen atoms (especially fluorine, chlorine or bromine) or alkyl groups. Preferably, at least one of these radicals is a hydrogen atom.

In general, the radicals R$^1$ to R$^7$ contain in total at least 5, preferably 12 to 40 carbon atoms. The molecular weight of the compound of the formula I is increased by these substituents in general by 60 to 800, preferably by 100 to 700, in particular by 200 to 600, compared with 9-phenylacridine.

Compounds in which at least one of the radicals R$^1$ to R$^7$ is or contains an aromatic group are preferred. In general, at least one of the radicals R$^2$ to R$^7$ is different from hydrogen, and preferably it is the radical R$^2$. Advantageously, compounds are also used which contain a halogen atom, in particular a fluorine, chlorine or bromine atom, in at least one of the substituents R$^1$ to R$^4$. Preferably, those substituents are used which contain (optionally in addition to the aromatic group) at least one oxygen atom which may be an ethereal, carbonyl or ester oxygen atom.

The compounds of the formula I may be present and be used in pure form or as mixtures with one another, for example as substance mixtures which are produced during the synthesis. Mixtures of this type usually have the advantage of a better solubility than the pure compounds in the coating solvents.

Some of the compounds of the formula I are already known, for example 2,7-dibenzoyl-9-phenylacridine from J. Org. Chem. 29, 2857 (1964) or from J. Chem. Soc. (London) C 1967, 2071 and 1968. 2900. No usability as photoinitiators is mentioned therein.

The compounds of the formula I are synthesized by reacting diphenylamine or its simple substitution products, for example 4,4'-dimethyldiphenylamine, 3-methyldiphenylamine or 4-chlorodiphenylamine, with benzoic acid or simple benzoic acid derivatives, for example tert-butylbenzoic acid, benzophenone-4-carboxylic acid, diphenyl-4-carboxylic acid, 4-aminomethylbenzoic acid or terephthalic acid in a suitable reaction medium such as polyphosphoric acid at about 150°–200° C.

With diphenylamine, acridine compounds of the formula I are obtained in which $R^1$ is an optionally substituted benzoyl group whose carbonyl group can be further reacted, for example, reduced to the —CHOH group with sodium boranate. A multiplicity of further derivatives is possible in the sequence: reaction of the OH group with acid anhydrides, isocyanates, condensation reactions with phenols or esterifications.

Examples of suitable compounds of the formula I are 2,7-dibenzoyl-9-phenylacridine, 2,7-bis(α-hydroxybenzyl)-9-phenylacridine, 2,7-bis(α-acetoxybenzyl)-9-phenylacridine, 2,7-dimethyl-9-(4-methylphenyl)acridine, 2,7-dimethyl-9-phenylacridine, 2,7-bis(3,4-dimethylbenzoyl)-9-(3,4-dimethylphenyl)acridine, 2,7-bis(α-acetoxy-4-tertbutylbenzyl)-9-(4-tert-butylphenyl)acridine, 2,7-dimethyl-9-(3,4-dichlorophenyl)acridine, 2,7-dimethyl-9-(4-benzoylphenyl)acridine, 2,7-bis(2-chlorobenzoyl)-9-(2-chlorophenyl)acridine, 2-(α-hydroxy-3-bromobenzyl)-6-methyl-9-(3-bromophenyl)acridine, 2,5-bis(4-tert-butylbenzoyl)-9-(4-tertbutylphenyl)acridine, 1,4-bis(2,7-dimethyl-9-acridinyl)benzene, 2,7-bis(α-phenylaminocarbonyloxy-3,4-dimethylbenzyl)-9-(3,4-dimethylphenyl)acridine and 2,7-bis(3,5-dimethyl-4-hydroxy-4'-fluorodiphenylmethyl)-9-(4-fluorophenyl)acridine.

The quantitative proportion of the compounds of the formula I in the mixture according to the invention is in general about 0.01 to 10, preferably 0.1 to 5% by weight, based on the nonvolatile constituents.

For the purposes of the invention, suitable polymerizable compounds are known and are described, for example, in U.S. Pat. Nos. 2,760,863 and 3,060,023.

Preferred examples are acrylic acid esters and methacrylic acid esters of monohydric or polyhydric, preferably at least dihydric alcohols such as ethylene glycol diacrylate, polyethylene glycol dimethacrylate, acrylates and methacrylates of trimethylolethane, trimethylolpropane, pentaerythritol and dipentaerythritol and of polyhydric alicyclic alcohols or N-substituted acrylic acid amides and methacrylic acid amides. Advantageously, reaction products of mono- or diisocyanates with partial esters of polyhydric alcohols are also used. Monomers of this type are described in DE-A 2,064,079, 2,361,041 and 2,822,190. The quantitative proportion of monomers in the coating is in general about 10 to 80, preferably 20 to 60% by weight.

The mixture also contains, in addition, a polymeric binder. A multiplicity of soluble organic polymers can be used as binder.

As examples, mention may be made of polyamides, polyvinyl esters, polyvinyl acetals, polyvinyl ethers, epoxy resins, polyacrylic acid esters, polymethacrylic acid esters, polyesters, alkyd resins, polyacrylamide, polyvinyl alcohol, polyethylene oxide, polydimethylacrylamide, polyvinyl pyrrolidone, polyvinylmethylformamide, polyvinylmethyl acetamide and also copolymers of the monomers which form the homopolymers listed.

Furthermore, natural substances or modified natural substances, for example gelatin and cellulose ethers, are possible as binders.

The use of binders which are water-insoluble but are soluble, or at least swellable, in aqueous alkaline solutions is particularly advantageous since coatings containing such binders can be developed with the preferred aqueous alkaline developers. Such binders may contain, for example, the following groups: —COOH, $PO_3H_2$, —$SO_3H$, —$SO_2NH$—, —$SO_2$—NH—$SO_2$— and —$SO_2$—NH—CO—.

As examples thereof, mention may be made of maleate resins, polymers of β-(methacryloyloxy)ethyl N-(p-tolylsulfonyl)carbamate and copolymers of the latter and similar monomers with other monomers, and also vinyl acetate/crotonic anhydride and styrene/maleic anhydride copolymers. Alkyl methacrylate/methacrylic acid copolymers and copolymers of methacrylic acid, higher alkyl methacrylates and methyl methacrylate and/or styrene, acrylonitrile etc., such as are described in DE-A 2,064,080 and 2,363,806, are preferred.

The quantity of binder is in general about 20 to 90, preferably 40 to 80% by weight of the constituents of the coating.

Depending on the planned application and depending on the desired properties, the photopolymerizable mixtures may contain diverse substances as additives.

Examples are: inhibitors for preventing thermal polymerization of the monomers, hydrogen donors, substances which modify the spectral photosensitivity of coatings of this type, dyestuffs, colored and colorless pigments, color formers, indicators, and plasticizers, for example polyglycols or esters of p-hydroxybenzoic acid.

These constituents are advantageously chosen in a manner such that they have as little absorption as possible in the actinic radiation range which is important for the initiation process.

For the purpose of this description, actinic radiation shall be understood to mean any radiation whose energy is equivalent at least to that of short wave visible light. Longwave UV radiation and also electron radiation, X-ray radiation and laser radiation are suitable.

The photopolymerizable mixture may be used for a wide variety of applications, for example to produce safety glass, lacquers which are cured by light or corpuscular beams, for example electron beams, in the field of dentistry and, in particular, as a photosensitive copying material in the field of reproduction.

The detailed description of the invention is restricted to the latter field of application, but the invention is not restricted thereto. As possible applications in this field, mention may be made of copying materials for the photomechanical production of print forms for letterpress printing, lithographic printing, gravure printing, screen printing, of relief images, for example production of texts in Braille, of single copies, tanned images, pigment images, etc. Furthermore, the mixtures may be used for the photomechanical production of etch resists, for example for manufacturing nameplates, printed circuits and for chemical milling. The mixtures according to the invention are particularly important as copying materials for the photomechanical production of lithographic print forms and for the photoresist techniques.

For the said application purposes, the mixture can be utilized commercially in the form of a liquid solution or dispersion, for example as a photoresist solution, which is applied by the user himself to an individual base, for example for chemical milling, for the production of printed circuits, of screen printing stencils and the like. The mixture may also take the form of a solid photosensitive coating on a suitable base in the form of a storable precoated photosensitive copying material, for example for production of print forms. It is also suitable for the production of dry resist.

It is in general beneficial to largely exclude the mixtures from the influence of atmospheric oxygen during the photopolymerization. If the mixture is used in the form of thin copying coatings, it is advisable to apply a suitable top coat which has low permeability to oxygen. The latter may be self-supporting and may be peeled off before the copying coating is developed. Polyester films, for example, are suitable for this purpose. The top coat may also be composed of a material which dissolves in the developer liquid or may be removed at least at the noncured points during development. Suitable materials for this purpose are, for example, waxes, polyvinyl alcohol, polyphosphates, sugar etc.

Suitable coating bases for copying materials produced with the mixture according to the invention are, for example, aluminum, steel, zinc, copper and plastic films, for example made of polyethylene terephthalate or cellulose acetate, and also screen printing bases such as perlon gauze.

The photosensitive materials using the mixture according to the invention are produced in a known manner.

Thus, the mixture can be taken up in a solvent and the solution or dispersion may be applied by pouring, spraying, immersion, application with rollers, etc. as a film to the base provided and then dried. Thick coatings (for example of 250 $\mu$m and over) are advantageously produced by extrusion or pressing as a self-supporting film which is then possibly laminated onto the base. In the case of dry resist, solutions of the mixture are applied to transparent temporary bases and dried. The photosensitive coatings (thickness approximately between 10 and 100 $\mu$m) are then laminated onto the desired final substrate, together with the temporary base.

The processing of the materials is carried out in a known manner. For the purpose of development, they are treated with a suitable developer solution, preferably a weakly alkaline aqueous solution, in which process the unexposed portions of the coating are removed and the exposed regions of the copying coating remain behind on the base.

The copying materials according to the invention are notable for a lower loss in photosensitivity during storage. This advantage is effected apparently by a higher resistance to diffusion of the initiators in the photopolymerizable coating compared with unsubstituted 9-phenylacridine. The diffusion resistance increases with increasing molecular weight. In this connection, it is essential that the substituents are in the 2-position or preferably in the 2,7-position of the acridine nucleus. The initiators also do not migrate, or migrate to a substantially lesser extent than known initiators, out of the photocured coating.

Examples of the mixture according to the invention are given below. Here the preparation of compounds of the formula I is first described. Then Table I specifies photoinitiators which are used in the photopolymerizable mixtures of the application examples.

In the examples, parts by weight (pbw) and parts by volume (pbv) are in the ratio of g to ccm. Unless otherwise specified, percentages and quantity ratios are understood in units of weight.

PREPARATION EXAMPLES 1. 2,7-Dibenzoyl-9-phenylacridine (compound 1)

1 pbw of diphenylamine and 15 pbw of polyphosphoric acid are heated to 100° C. while stirring. After adding 2.5 pbw of benzoic acid, heating of the mixture is continued at 200° C. for 45 minutes. After cooling to 100° C., the mixture is poured into 70 pbw of water, the product is filtered off and purified (m.p. 210° C.).

2. 2,7-Bis($\alpha$-hydroxybenzyl)-9-phenylacridine (compound 2)

1 pbw of 2,7-dibenzoyl-9-phenylacridine is suspended in 4 pbw of ethanol and reduced by adding 0.1 pbw of sodium boranate in portions at 20°–50° C. After 24 hours, the reaction product is precipitated with water, purified and dried (m.p. above 280° C.).

3. 2,7-Bis($\alpha$-acetoxybenzyl)-9-phenylacridine (compound 3)

1 pbw of 2,7-bis($\alpha$-hydroxybenzyl)-9-phenylacridine is suspended in 4 pbw of acetone and heated for 1 hour under reflux with 0.8 pbw of acetic anhydride and 0.001 pbw of 4-dimethylaminopyridine. Water is then added to the mixture and the product is filtered off.

4. 2,7-Dimethyl-9-(p-tolyl)acridine (compound 4)

1 mol of 4,4'-dimethyldiphenylamine and 1 mol of 4-methylbenzoic acid are heated for 1 hour at 200° C. in 5000 g of polyphosphoric acid. After cooling, water and ammonia are added to the reaction mixture and the product is filtered off by suction and purified (m.p. 210°–211° C.).

Table

| Compounds of the formula I having $R^3 = R^4 = R^7 = H$ | | | | |
| --- | --- | --- | --- | --- |
| Compound | $R^1$ | $R^2$ | $R^5$ | $R^6$ |
| 1 | Benzoyl | Benzoyl | H | H |
| 2 | $\alpha$-Hydroxybenzyl | $\alpha$-Hydroxybenzyl | H | H |
| 3 | $\alpha$-Acetoxybenzyl | $\alpha$-Acetoxybenzyl | H | H |
| 4 | Methyl | Methyl | 4-Methyl | H |
| 5 | Methyl | Methyl | H | H |
| 6 | 3,4-Dimethylbenzoyl | 3,4-Dimethylbenzoyl | 4-Methyl | 3-Methyl |
| 7 | $\alpha$-Acetoxy-p-tert-butylbenzyl | $\alpha$-Acetoxy-p-tert-butylbenzyl | 4-tert-butyl | H |

APPLICATION EXAMPLE 1

The following three coating solutions were prepared from 50 pbw of a terpolymer of methyl methacrylate, n-hexylmethacrylate and methacrylic acid (5:60:35) with a mean molecular weight $M_w = 70,000$, 11 pbw of the diurethane formed from 2 mol of hydroxyethyl methacrylate and 1 mol of 2,2,4-trimethylhexamethylene diisocyanate, 39 pbw of the reaction product formed from 1 mol of hydroxyethyl acrylate, 2 mol of caprolactone and 1 mol of n-butyl isocyanate.

0.1 pbw of the blue dyestuff 1,4-bis-isobutylaminoanthraquinone (C.I. 61551), 160 pbw of butanone and 40 pbw of ethanol, to which a—0.51 pbw of 9-phenylacridine (molecular weight 255, comparison)

b—0.926 pbw of compound (molecular weight 464), or c—1.102 pbw of compound 3 (molecular weight 552)

were added as photoinitiator.

The solutions were applied to biaxially oriented and heat-set polyethylene terephthalate films having a thickness of 25 μm in a manner such that a coating weight of 45 g/m² was always obtained after drying at 100° C.

To protect the dry resist coatings from contamination with dust and against damage, they were clad with a 23 μm thick polyethylene top film and rolled up. They can then be stored with light excluded for a prolonged period of time. The rolls (polyethylene film outwards) were fastened with a commercial adhesive tape.

After the rolls had been stored for 24 hours at 40° C., the resists were processed.

On peeling off the adhesive tape it was found that, although separated from the resist by the polyethylene top film, the tape was colored light blue by anthraquinone dyestuff which had diffused. In order to test whether the adhesive tape also contained traces of photoinitiators, a UV spectrum was recorded at 350–450 nm using a spectrophotometer, type Perkin-Elmer Lambda 3. Compared with a comparison sample, the adhesive tape of sample a exhibited a peak (extinction=0.12) at 358 nm. The light blue adhesive tapes b and c exhibited no additional extinction between 350 and 450 nm. They did not contain any photoinitiator.

The dry resist films were laminated in a commercial laminating apparatus at 115° C. onto phenolic laminate panels clad with copper foil having a thickness of 35 μm and were exposed for 4 seconds by means of a 5 kW metal halide lamp with a distance of 110 cm between lamp and vacuum copying frame. The master used was a 13-step exposure wedge which contained density increments of 0.15. In this operation, the exposure wedge was sited so that it was positioned on the parts which had originally been covered by polyethylene film and adhesive tape.

After exposure, the polyester films were peeled off and the coatings were developed with a 1%-strength sodium carbonate solution in a spray development apparatus in the course of 60 s.

The sample a was underexposed, the resist being cured only up to step 5; lines reproduced were 10% too narrow. The step wedge of samples b and c, on the other hand, was fully cured up to step 6. A test master having 80 μm wide clear and dark lines was reproduced true to scale as a raised image.

APPLICATION EXAMPLE 2 a—0.70 pbw of 9-(3,4-dimethylphenyl)acridine (molecular weight 283, comparison), b—0.70 pbw of compound 5 (molecular weight 283), or c—1.35 pbw of compound 6 (molecular weight 547)

were dissolved as photoinitiators in coating solutions composed of 40 pbw of a copolymer of methyl methacrylate and methacrylic acid (acid number 115), 40 pbw of trimethylolpropane triacrylate and 0.5 pbw of Disperse Blue 134 (C.I. 61551) in 520 pbw of 2-methoxyethanol.

The solutions were applied by spinning to electrolytically roughened 0.3 mm thick aluminum which had been hardened by anodizing. The coating was dried for 2 minutes at 100° C., a coating weight of 2.4 g/m² being obtained.

For the purpose of protection against contamination, the coated, slightly sticky photosensitive panels were clad at room temperature with a 20 μm thick polyethylene film.

The printing plates thus obtained were exposed for 15 seconds with a 5 kW metal halide lamp at a distance of 110 cm under a negative master together with a 13-step exposure wedge which contained density increments of 0.15.

The parts not cured by light were removed by wiping over with a developer solution of the following composition:

3 pbw of sodium metasilicate nonahydrate, 0.05 pbw of strontium chloride, 0.03 pbw of nonionogenic wetting agent (coconut butter alcohol/polyoxyethylene ether containing approx. 8 oxyethylene units), 0.003 pbw of antifoaming agent, 100 pbw of demineralized water.

The number of completely cured steps of the exposure wedge provides a coefficient of measurement for the photosensitivity. The values are listed under (A) in the table below.

In order to elucidate the diffusion of the initiator through the polyethylene film, a commercial colorless transparent adhesive tape was pressed onto the polyethylene film on one sample panel in each case and the composite was stored for 24 hours at room temperature (23° C.). The adhesive film was then peeled off again and (B) the increase in the optical density at 358 nm was measured. The exposure test wedge having 13 gray steps was furthermore placed at the position where the adhesive film had been removed (experiment C), and the printing plate was exposed for 15 seconds and then developed just as described above. The results listed in the following table show that the initiator diffuses most strongly out of the sample a, to a markedly lesser extent out of sample b and does not diffuse out of sample c.

|   | (A) Wedge steps | (B) Density difference | (C) Wedge step |
|---|---|---|---|
| a | 6 | 0.17 | 2 |
| b | 7 | 0.11 | 4 |
| c | 7 | 0 | 7 |

EXAMPLE 3 a—1 pbw of compound 7 or b—1 pbw of isopropylthioxanthone and 2 pbw of p-dimethylaminobenzoate (initiator mixture of a commercial photoresist)
were added as initiators to coating solutions composed of:
65 pbw of a copolymer of methyl methacrylate, butyl acrylate, styrene and methacrylic acid (35:40:5:20),
35 pbw of trimethylolpropane triacrylate,
1 pbw of leuco crystal violet and
0.05 pbw of crystal violet in
75 pbw of butanone and
75 pbw of ethanol.

The solutions were applied to polyethylene terephthalate film as in Example 1, dried, laminated onto copper foil, exposed and developed. Then the optimum exposure time was determined.

In a further experiment, boards produced and developed as above were rinsed for 30 s with tap water, incipiently etched for 30 s in a 15% strength ammonium peroxodisulfate solution, rinsed with water again, immersed for 30 s in 10%-strength sulfuric acid and then electroplated consecutively in the following electrolyte baths.

1. 60 minutes in copper electrolyte bath
   supplied by Schloetter, Geislingen/Steige,
   "bright copper bath" type
   current density: 2.5 A/dm²
   metal buildup: approx. 30 m
   temperature: room temperature
2. 15 minutes in a lead-tin bath LA supplied by
   Schloetter, Geislingen/Steige,
   current density: 2 A/dm²
   metal buildup: 15 μm
   temperature: room temperature The plates did not exhibit any undercutting or damage.

To test whether the resist constituents diffuse into the electroplating baths, 0.075m² glass plates were coated with resist (45 g/m²) and immersed for one hour in one liter of 20%-strength sulfuric acid. In both cases the sulfuric acid remained colorless: a UV spectrum (200–800 nm) of both sulfuric acid extracts was then recorded with the spectrophotometer (1 cm cell); b showed a distinct peak at 225 nm (extinction=0.95), some of the initiator system having migrated into the sulfuric acid; a showed no contamination.

What is claimed is:

1. A photopolymerizable mixture which comprises:
   a) a polymeric binder,
   b) a polymerizable compound having at least one terminal olefinic double bond and having a boiling point above 100° C. at normal pressure, and
   c) a 9-arylacridine compound as photoinitiator,
   wherein the acridine compound conforms to the general formula (I)

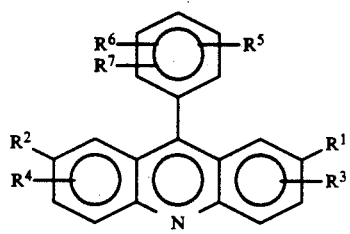

(I)

in which
R¹ and R² are identical or different and denote an optionally substituted alkyl or acyl group,
R³ and R⁴ are identical or different and denote hydrogen or halogen atoms or optionally substituted alkyl or acyl groups,
R⁵, R⁶, and R⁷ are identical or different and denote hydrogen or halogen atoms or optionally substituted alkyl, aryl or acyl groups, or groups of the formula II

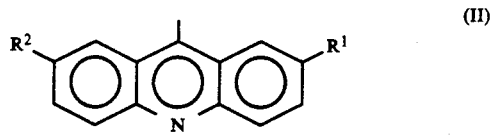

(II)

2. A photopolymerizable mixture as claimed in claim 1, wherein R¹ is an alkyl group containing 1 to 10 carbon atoms, an aliphatic acyl group containing 2 to 10 carbon atoms or an aromatic acyl group containing 7 to 15 carbon atoms.

3. A photopolymerizable mixture as claimed in claim 1, wherein R³, R⁴ and R⁵ are hydrogen atoms.

4. A photopolymerizable mixture as claimed in claim 1, wherein the radicals R¹ to R⁷ together contain at least 6 carbon atoms.

5. A photopolymerizable mixture as claimed in claim 1, wherein at least one of the radicals R¹ to R⁷ contains an aromatic group.

6. A photopolymerizable mixture as claimed in claim 1, wherein at least one of the radicals R³ to R⁷ is different from hydrogen.

7. A photopolymerizable mixture as claimed in claim 1, wherein the radicals R¹ to R⁷ together increase the molecular weight of the compound of the formula I by about 60 to 800.

8. A photopolymerizable mixture as claimed in claim 7, wherein the radicals R¹ to R⁷ together increase the molecular weight of the compound of the formula I by 100 to 700.

9. A photopolymerizable mixture as claimed in claim 1, wherein at least one of the radicals R¹ to R⁷ contains an oxygen atom.

10. A photopolymerizable mixture as claimed in claim 1, wherein the binder is insoluble in water and soluble in aqueous alkaline solutions.

11. A photopolymerizable mixture as claimed in claim 1, wherein the photopolymerizable compound is an ester of acrylic acid or methacrylic acid with an aliphatic alcohol.

12. A photopolymerizable mixture as claimed in claim 1, wherein the proportion of the compounds of the formula I is about 0.01 to 10 wt %, based on the nonvolatile constituents of the mixture.

13. A photopolymerizable copying material as claimed in claim 12, further comprising a layer having a low permeability to oxygen disposed on top of said photopolymerizable coating.

14. A photopolymerizable copying material comprising a coating base and a photopolymerizable coating, wherein the coating comprises a mixture as claimed in claim 1.

15. A photopolymerizable as claimed in claim 1, consisting essentially of the polymeric binder, the polymerizable compound and the 9-arylacridine compound.

* * * * *